United States Patent
De Witte

(10) Patent No.: US 7,297,477 B2
(45) Date of Patent: Nov. 20, 2007

(54) METHODS AND COMPOSITIONS FOR DETECTING VIRAL NUCLEIC ACID IN A CELL

(75) Inventor: Anniek De Witte, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/353,719

(22) Filed: Feb. 13, 2006

(65) Prior Publication Data

US 2007/0190618 A1   Aug. 16, 2007

(51) Int. Cl.
*C12Q 1/70* (2006.01)

(52) U.S. Cl. ......................................................... 435/5

(58) Field of Classification Search .............. 536/23.1, 536/24.3, 24.31, 24.32
See application file for complete search history.

(56) References Cited

U.S. PATENT DOCUMENTS

| | | | |
|---|---|---|---|
| 6,251,601 B1 | 6/2001 | Bao et al. | |
| 6,410,243 B1 | 6/2002 | Wyrick et al. | |
| 6,511,808 B2 | 1/2003 | Wolffe et al. | |

OTHER PUBLICATIONS

Ghedin et al., "Use of a Multi-virus Array for the Study of Human Viral and Retroviral Pathogens: Gene Expression Studies and ChIP-chip Analysis," Retrovirology 2004, 1:10.

Guillaud-Bataille et al., "Detecting Single DNA Copy Number Variations in Complex Genomes Using One Nanogram of Starting DNA and BAC-array CGH,", Nucleic Acids Research, 2004, vol. 32, No. 13, e112.

Iyer et al., "Genomic Binding Sites of the Yeast Cell-cycle Transcription Factors SBF and MBF," Nature, vol. 409, Jan. 25, 2001, p. 533-538.

Lee et al., "Transcriptional Regulatory Networks in *Saccharomyces cerevisiae*," Science, vol. 298, Oct. 25, 2002, p. 799-804.

Lieb et al., "Promoter-specific Binding of Rap1 Revealed by Genome-wide Maps of Protein-DNA Association," Nature Genetics, vol. 28, Aug. 2001, p. 327-334.

Lythgo, "Molecular Virology of HIV-1 and Current Antiviral Strategies," BioTeach Journal, vol. 2, Fall 2004, p. 81-87.

Ren et al., "Genome-Wide Location and Function of DNA Binding Proteins," Science, vol. 290, Dec. 22, 2000, p. 2306-2309.

Rodriguez et al., "Tilling the Chromatin Landscape: Emerging Methods for the Discovery and Profiling of Protein-DNA Interactions," Biochem. Cell Biol. 83: 525-534 (2005).

*Primary Examiner*—Bruce R. Campell
*Assistant Examiner*—Nicole E Kinsey

(57) ABSTRACT

Methods and compositions for identifying or detecting viral nucleic acids in a host cell are described. DNA fragments are bound to DNA-binding protein in a host cell and enriched using immunoprecipitation. The enriched fragments are then hybridized to a microarray containing sequences complementary to proviral DNA and genomic DNA.

9 Claims, 6 Drawing Sheets

METHODS AND COMPOSITIONS FOR DETECTING VIRAL NUCLEIC ACID IN A CELL

BACKGROUND

Retroviruses are major pathogens that can affect all vertebrates causing an extremely wide range of responses in infected animal hosts. For example, one of the most potent and lethal retroviruses is HIV-1, the agent that causes AIDS. Retroviruses are a large and diverse family of viruses that replicate by a unique process that is significantly different from other forms of viruses. The virion particles that make up retroviruses contain (+) strand genomic RNA. When the retrovirus enters a host cell, the (+) strand RNA is converted into double-stranded DNA through action of the enzyme reverse transcriptase (RT). This double-stranded DNA copy of the viral genome is called proviral DNA. The proviral DNA is then integrated into the host chromosomal DNA for replication by the action of the enzyme integrase (IN). Integration links the ends of linear proviral DNA to host genomic DNA. In a productive infection, proviral DNA acts as a template for the formation of retroviral particles and transcription of viral proteins, through the action of host RNA polymerase II. As integration of proviral DNA is necessary for replication, infected cells without integrated proviral DNA cannot spread infection. The formation of the integrated provirus is believed responsible for maintaining a persistent infection, for permanent entry into the host germ line and for mutagenic or oncogenic activities.

Current methods, licensed and approved by the FDA, for study of retroviruses such as HIV, include antibody-based assays, where antibodies are detected using ELISA (enzyme linked immunosorbent assay) or EIA (enzyme immunoassay) methods. PCR-based methods have also been used to study retroviruses. In these assays, DNA is detected by PCR amplification with virus-specific primers.

SUMMARY

This patent relates to methods for identifying or detecting a viral nucleic acid in a host cell. In the methods described herein, DNA fragments generated from the host cell are enriched by immunoprecipitation. The enriched DNA is then hybridized to a microarray comprising sequences complementary to proviral and genomic DNA. Actively transcribed viral proteins in the host cell can be identified using the methods provided herein.

Another aspect provides DNA arrays that can be used to identify viral nucleic acids in a host cell, or the location on the genome where a virus would integrate. In an embodiment, the arrays contain probe sequences complementary to both proviral DNA and host cell genomic DNA. The arrays can be used to the presence of a productive viral infection. The arrays can also be used to determine the location of integration of a virus into the host cell genome.

In another aspect, kits that include arrays and compositions for identifying or detecting viral nucleic acids in a host cell are provided. The kits include one or more arrays containing probe sequences to viral and genomic DNA, along with reagents necessary for immunoprecipitation, amplification and labeling.

DETAILED DESCRIPTION

Figure 1:
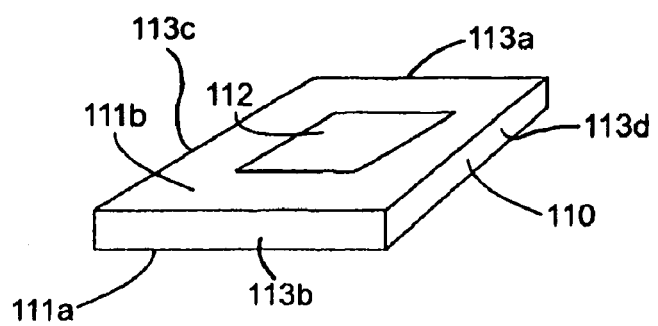
FIG. 1 shows an exemplary substrate carrying an array, such as may be used in the devices described herein.

Various embodiments will be described in detail with reference to the drawings, wherein like reference numerals represent like parts throughout the several views. Reference to various embodiments does not limit the scope of the claims attached hereto. Additionally, any examples set forth in this specification are not intended to be limiting and merely set forth some of the many possible embodiments for the claims.

Unless defined otherwise, all technical and scientific terms used herein have the same meaning as commonly understood to one of ordinary skill in the art. Although any methods, devices and material similar or equivalent to those described herein can be used in the practice or testing of the methods herein, the methods, devices and materials are now described.

All publications and patent applications in this specification are indicative of the level of ordinary skill in the art and are incorporated herein by reference in their entireties.

The term "genome" refers to all nucleic acid sequences (coding and non-coding) and elements present in or originating from a single cell or each cell type in an organism. The term genome also applies to any naturally occurring or induced variation of these sequences that may be present in a normal, mutant or disease variant of any virus or cell type. These sequences include, but are not limited to, those involved in the maintenance, replication, segregation, and higher order structures (e.g. folding and compaction of DNA in chromatin and chromosomes), or other functions, if any, of the nucleic acids as well as all the coding regions and their corresponding regulatory elements needed to produce and maintain each particle, cell or cell type in a given organism. For example, eukaryotic genomes in their native state have regions of chromosomes protected from nuclease action by higher order DNA folding, protein binding, or subnuclear localization. The methods described herein can be used to identify these protected regions in a genome-wide (high throughput) fashion.

For example, the human genome consists of approximately $3 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of chromosome Xs (female) for a total of 46 chromosomes. A genome of a cancer cell may contain variable numbers of each chromosome in addition to deletions, rearrangements and amplification of any subchromosomal region or DNA sequence.

A "host cell" is a cell that has been infected with a virus or other microorganism. Viruses use host cells as a part of their life cycles, using the processes of the host cell to reproduce themselves. The host cells include, but are not limited to, eukaryotic cells, mammalian cells, etc.

The term "retrovirus" refers to a member of a class of viruses that have their genetic material in the form of RNA and use the reverse transcriptase enzyme to translate their RNA into DNA in the host cell.

The term "provirus" refers to a virus that has integrated itself into the host cell. The term "proviral DNA" refers to the DNA of a virus that is inserted into the host cell genome in an infected cell. The terms "provirus" and "proviral DNA" are used interchangeably herein.

A "latent infection" occurs when viral DNA is inserted into a host cell, but viral proteins are not actively transcribed. As a result, no symptoms or other visual manifestations of a viral infection occur. A "productive infection" or a "virulent infection" occurs when, following integration of the virus into the host cell genome, viral proteins are actively produced, resulting in pathogenicity. The terms "productive infection" and "virulent infection" are used interchangeably herein.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "sample" as used herein relates to a material or mixture of materials, typically, although not necessarily, in fluid form, containing one or more components of interest. Samples include, but are not limited to, biological fluid samples containing eukaryotic or mammalian host cells. Such samples may be derived from natural biological sources such as cells or tissues. A "biological fluid" includes, but is not limited to, blood, plasma, serum, saliva, cerebrospinal fluid, amniotic fluid, etc., as well as fluid collected from cell culture medium, etc.

The term "DNA-binding protein" is any protein that binds to double- or single-stranded DNA including, but not limited to, many proteins involved in the regulation of gene expression (including transcription factors), proteins involved in the packaging of DNA within the nucleus (such as histones), nucleic acid dependent-polymerases involved in DNA replication and transcription, proteins involved in viral transcription and integration, or any of many accessory proteins which are involved in these processes.

The terms "cleavage," "cleaving," and "cleaved" refer to the splitting or cutting of molecules, including any complex formed by binding of DNA with DNA-binding protein. The molecules may be cut or split by the action of restriction enzymes, or by shearing using mechanical means, such as shearing by sonication, for example.

The term "array" encompasses the term "microarray" and refers to an ordered array presented for binding to nucleic acids and the like. Arrays, as described in greater detail below, are generally made up of a plurality of distinct or different features. The term "feature" is used interchangeably herein with the terms: "features,""feature elements," "spots," "addressable regions," "regions of different moieties," "surface or substrate immobilized elements" and "array elements," where each feature is made up of oligonucleotides bound to a surface of a solid support, also referred to as substrate immobilized nucleic acids.

An "array," includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. In the broadest sense, the arrays of many embodiments are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus).

In those embodiments where an array includes two more features immobilized on the same surface of a solid support, the array may be referred to as addressable. An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "probe" may be the one that is to be evaluated by the other (thus, either one could be an unknown mixture of analytes, e.g., polynucleotides, to be evaluated by binding with the other).

A "scan region" refers to a contiguous (preferably, rectangular) area in which the array spots or features of interest, as defined above, are found. The scan region is that portion of the total area illuminated from which the resulting fluorescence is detected and recorded. For the purposes of this disclosure, the scan region includes the entire area of the slide scanned in each pass of the lens, between the first feature of interest, and the last feature of interest, even if there are intervening areas that lack features of interest.

An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

The term "substrate" as used herein refers to a surface upon which marker molecules or probes, e.g., an array, may be adhered. Glass slides are the most common substrate for biochips, although fused silica, silicon, plastic, flexible web and other materials are also suitable.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

In this specification and the appended claims, the singular forms "a," "an" and "the" include plural reference unless the context clearly dictates otherwise. Unless defined otherwise, all technical and scientific terms used herein have the same meaning as commonly understood by one of ordinary skill in the art.

Methods for detecting the presence of viral nucleic acids in a host cell are provided herein. Nucleic acid fragments obtained from host cells are enriched and then hybridized to microarrays that contains probes for genomic DNA, as well as probes for viral nucleic acids. Hybridization to particular probe sequences on the microarray determines the presence or absence of viral nucleic acids.

Methods for determining whether viral nucleic acids are present in a host cell are described herein. In embodiments, the methods are used to detect the presence of viral DNA in a host cell, by exploiting the binding of DNA to a protein of interest. Viral DNA fragments or host cell genomic DNA fragments bound to the protein can be generated by various methods. In an embodiment, formaldehyde is used to fix the cells, and results in crosslinking of DNA-binding proteins to DNA. In another embodiment, UV light is used for crosslinking. In an aspect, the fixed cells are lysed and the resultant crude cell extracts are sonicated to shear the DNA. In an aspect, extensive sonication is used to produce uniformly sized fragments of DNA, typically about 1 kb. The generated fragments are fragments of DNA bound to the DNA-binding protein of interest.

In embodiments, the methods described herein can be used to detect or identify viral nucleic acids present in a host cell. Various methods can be used to enrich or isolate viral or host cell genomic DNA fragments bound to a protein of interest from a mixture containing both bound and unbound DNA fragments. In an embodiment, DNA fragments are enriched by immunoprecipitation, using an antibody that specifically binds to the protein of interest. If the protein of interest is associated with a specific region of the host cell genome, DNA fragments bound to that region of the genome will be enriched, relative to DNA fragments that do not bind to the protein of interest. In an aspect, the antibody is either monoclonal or polyclonal. In another aspect, an antigen-binding fragment of the particular antibody is used. In an aspect, the antibody or antigen-binding fragment is specific for proteins that are actively transcribed during a productive viral infection. In another aspect, the antibody or antigen-binding fragment is specific for proteins that are active in integration of viral DNA into the host cell genome. Antibodies used in the described methods are commercially available.

In the methods described herein, enriched and unenriched DNA fragments obtained from an infected host cell are used to identify viral nucleic acids. In an embodiment, enriched or isolated DNA fragments are purified and them amplified. Various methods for amplification can be used. including, but not limited to, PCR methods. In an aspect, the DNA fragments are amplified using ligation-mediated polymerase chain reaction (LM-PCR), which can reproducibly amplify even small quantities of DNA.

The presence of viral nucleic acids is detected by probing the isolated or enriched DNA fragments with oligonucleotide sequences complementary to viral DNA or host cell genomic DNA sequences. In an embodiment, the isolated DNA fragments are hybridized to the probes that are immobilized on a glass slide or microchip (i.e. a DNA microarray). In an aspect, a microarray contains spots or features corresponding to the viral DNA and host cell genomic DNA probe sequences. In another aspect, the probe sequences for proviral DNA and host cell genomic DNA are located on separate microarrays. Where a single microarray is used, enriched and unenriched DNA fragments can be differentially labeled using, for example, fluorophores such as Cy3 and Cy5. Comparison of the relative positions and intensities of the fluorophores on the microarray helps detect the presence of viral nucleic acids.

The present methods are for detecting and analyzing a wide variety of viruses that undergo reverse transcription to produce a provirus including, but not limited to, retroviruses. After a host cell is infected, proviral DNA can exist in either a latent or productive state. Proviral DNA refers to DNA from a viral source that has been incorporated into the host cell genome. Whether a provirus is in the latent or virulent state depends on a number of factors, including the production of specific proteins by the infected host cells. Accordingly, in one aspect, the method of can be used to examine proviral DNA in either the latent state or the virulent state.

In addition, this disclosure describes methods for detecting the integration of viral DNA into a host cell genome. Many viruses, including retroviruses and DNA tumor viruses undergo integration. After the RNA genome of the virus is reverse transcribed into a DNA genome, it is integrated into the genomic DNA of the host cell, through the action of the integrase enzyme. This integration event provides a tag that marks a particular time in evolution and can be used as a way to study speciation, divergence, etc. The integration event can be used to determine the mode of action of antiviral drugs, such as integrase inhibitors, for example.

The subject matter described herein is directed to methods for distinguishing a latent viral infection from a productive viral infection. In particular, the description herein relates to a method for detecting a virulent infection in a host cell. In an embodiment, DNA binding proteins are crosslinked to proviral DNA (if present) and genomic DNA in a host cell. The DNA bound by protein and DNA that remains unbound are cleaved to generate DNA fragments that contain DNA-binding protein bound to genomic DNA and/or proviral DNA. In a portion of the sample, the DNA fragments are enriched by immunoprecipitation. The enriched DNA fragments are isolated from the protein, amplified and labeled. The amplified and labeled fragments are then hybridized to an array containing oligonucleotides complementary to either proviral DNA or host genomic DNA. Enriched DNA fragments that selectively hybridize to oligonucleotides complementary to proviral DNA are used to indicate a virulent infection.

The methods herein can be used to detect and analyze latent and virulent states of multiple retroviruses at the same time. For example, the method can be used to identify particular HIV strains infecting a patient and whether the virus is in its latent or virulent state. Alternatively, the methods can be used to determine whether the presence of proviral DNA influences transcription of other genes. Therefore, the methods provide an effective and high-throughput screening tool for retrovirus activity.

The present description is directed also to methods for studying the integration of viral DNA in the genome. In an embodiment, viral DNA binding proteins are crosslinked to proviral DNA (if present) and genomic DNA in a host cell. The DNA bound by protein and DNA that remains unbound are cleaved to generate DNA fragments that contain DNA-binding protein bound to proviral DNA or genomic DNA. The DNA fragments are isolated from the protein, and amplified and labeled. The amplified and labeled fragments are then hybridized to DNA with sequences complementary to either proviral DNA or host genomic DNA sequences. DNA fragments that selectively hybridize to proviral DNA sequences are used to identify proviral DNA that has been integrated into the host genome. In a further embodiment, DNA fragments that selectively hybridize to proviral DNA sequences are used to identify the location on the host genome where the proviral DNA is integrated (i.e. the integration site).

The methods described herein can be used to analyze the mutagenic activity of retroviruses. For example, the insertion of proviral DNA into the host genome causes gross alterations in the genome. If such an insertion leads to tumor formation, the methods described herein can be used to determine the location of proviral insertion and thereby identify new oncogenes. The methods described herein provide an effective tool for detecting genetic alterations and the effect of such alterations on normal cell growth and metabolism.

In embodiments, methods for detecting and distinguishing between non-infected, latent viral infection and virulent/productive viral infections in a DNA sample are described below.

In an embodiment, the methods are used to detect proviral DNA, either in the latent or productive state in a sample from a host organism. DNA binding proteins are crosslinked to proviral DNA (if any) and genomic DNA in the sample. In a portion of the sample, the DNA fragments are enriched by immunoprecipitation with an antibody against a protein that is actively transcribed in an infected host cell. In an aspect, the DNA fragments are enriched by immunoprecipitation with an antibody against RNA polymerase II, or its subunits or helpers. The crosslinking is reversed and the enriched DNA is amplified and labeled. In another portion of the sample, the DNA that has not been enriched by immunoprecipitation is amplified and labeled. Both enriched and unenriched pools of labeled DNA are probed for hybridization to complementary genomic and proviral DNA. In an embodiment, one or more microarrays are used to probe for hybridization to complementary genomic and proviral DNA in the enriched and unenriched pools of labeled DNA. In a further embodiment, the enriched and unenriched pools of DNA are differentially labeled, using fluorophores such as Cy5 or Cy3, for example, and the labeled pools of DNA are then hybridized to a single DNA microarray including both proviral sequences and genomic sequences. In a still further embodiment, stringent hybridization conditions are employed.

Figure 4:
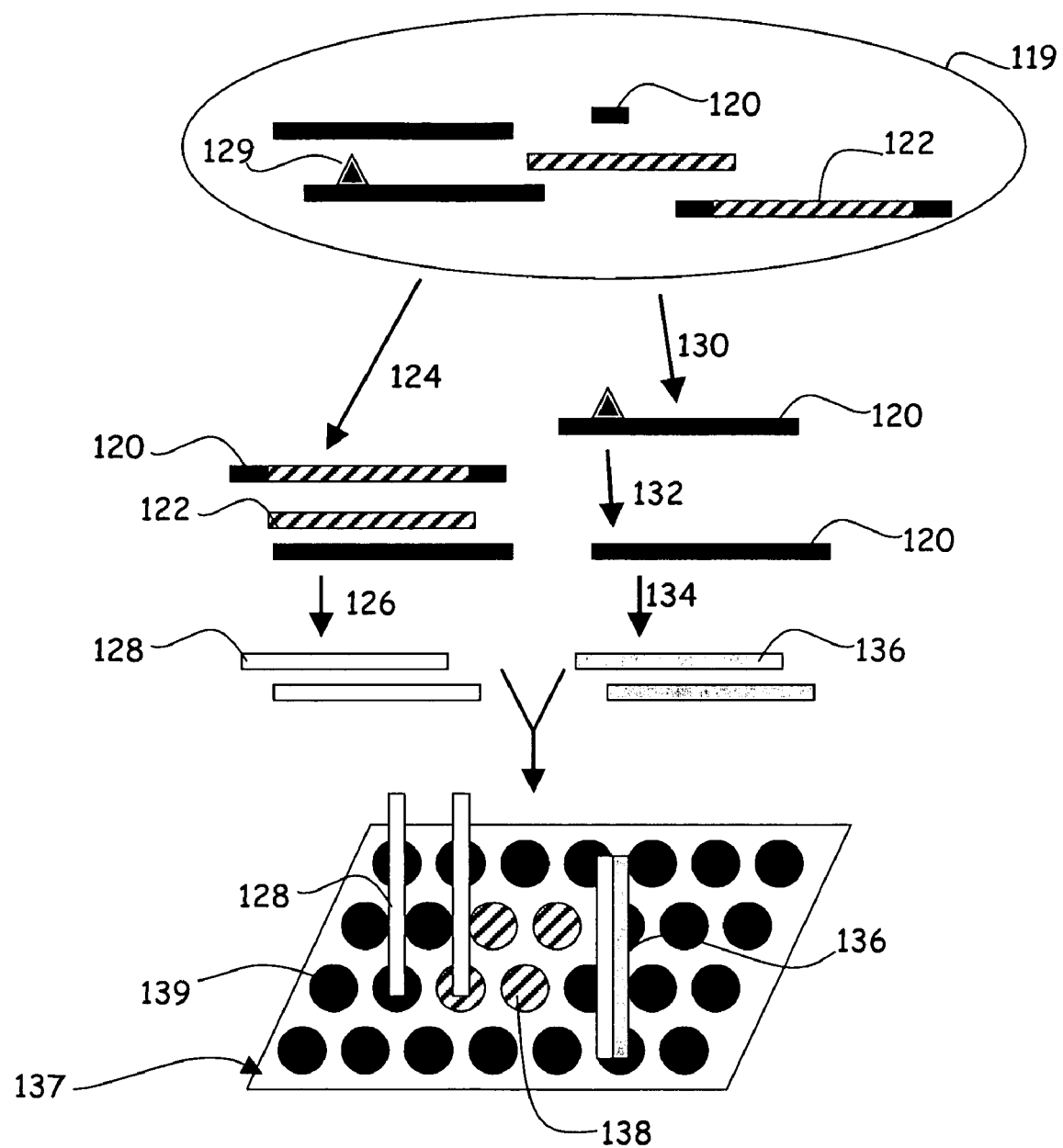
FIG. 4 shows a graphical illustration of a method, as provided herein, in the case of a latent viral infection.

In an embodiment, latent retroviral infection is detected in a sample comprising genomic DNA according to the method illustrated in FIG. 4. The sample DNA 119 being tested contains both host (genomic) DNA 120 and proviral DNA 122. A first portion of the sample DNA is amplified by LM-PCR (represented by arrow 124), and labeled with a first label (arrow 126) resulting in first labeled DNA fragments 128. A second portion of the sample DNA is cross-linked to DNA-bound proteins including RNA polymerase II 129 and immunoprecipitated with an anti-RNA Polymerase II antibody (arrow 130). Following immunoprecipitation, the cross-links are reversed and the DNA fragments are amplified by LM-PCR (arrow 132). The amplified DNA is labeled with a second label (arrow 134), resulting in second labeled DNA fragments 136. The first labeled DNA fragments 128 and the second labeled DNA fragments 136 are pooled and hybridized to an array 137 including both proviral sequences 138 and genomic sequences 139. In another embodiment (not shown), the first DNA fragments are hybridized to an array that includes only proviral sequences. The second pool of DNA fragments are hybridized to a second array that includes only genomic sequences. In such an embodiment, the DNA fragments can be, but do not have to be, labeled. In yet another embodiment, the first pool of DNA fragments is hybridized to a microarray including both proviral DNA and genomic DNA sequences and an image is obtained. The array is then stripped and then the second pool of DNA fragments is hybridized to the same array. The images obtained from the two hybridizations are compared.

Where the sample is from a host that has a latent retroviral infection, analysis of the array shows the following. The first labeled DNA fragments 128 hybridize to both genomic and proviral sequences on the array. The hybridization of the unenriched fragments 128 to the proviral sequences on the array indicates the presence of proviral DNA in the sample. The second labeled DNA fragments 136, enriched by immunoprecipitation with RNA polymerase II, only hybridize to host genomic sequences, and not to proviral sequences on the microarray. This indicates latent retroviral infection because, although the viral DNA is present, it is not actively transcribed.

Figure 5:
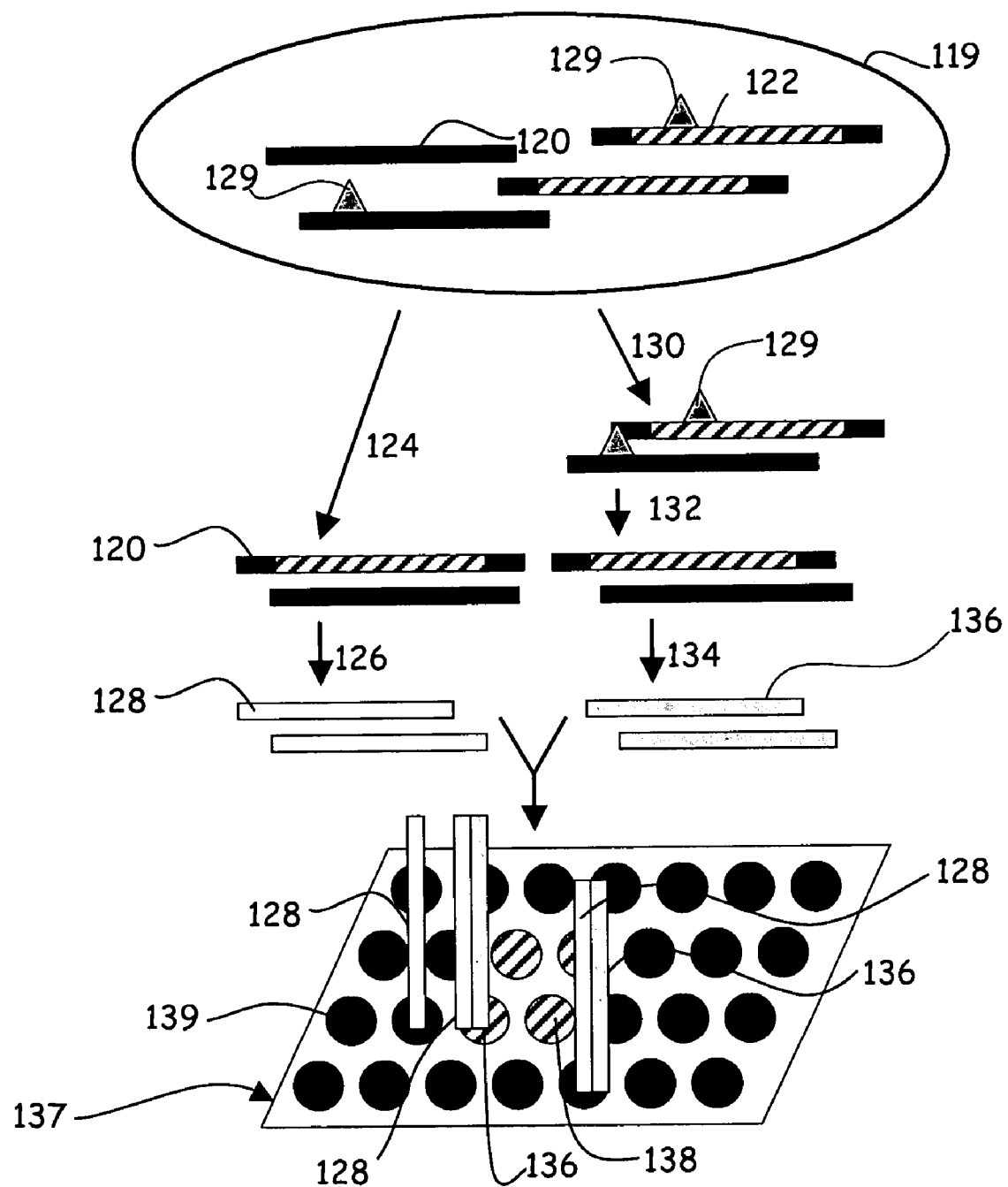
FIG. 5 shows a graphical illustration of a method, as provided herein, in the case of a virulent viral infection.

In an embodiment, productive retroviral infection is detected in a sample containing genomic DNA according to the method illustrated in FIG. 5. The sample DNA 119 being tested contains both host (genomic) DNA 120 and proviral DNA 122. A first portion of the sample DNA is amplified (represented by arrow 124), and labeled with a first label (arrow 126) resulting in first labeled DNA fragments 128. A second portion of the sample DNA is cross-linked to DNA-bound proteins including RNA polymerase II 129 and immunoprecipitated with an anti-RNA Polymerase II antibody (arrow 130). Following immunoprecipitation, the cross-links are reversed and the DNA fragments are amplified (arrow 132). The amplified DNA is labeled with a second label (arrow 134), resulting in second labeled DNA fragments 136. The first labeled DNA fragments 128 and the second labeled DNA fragments 136 are pooled and hybridized to an array 137 providing both proviral sequences 138 and genomic sequences 139.

Where the sample is from a host that has a productive retroviral infection, analysis of the array data shows the following. The first labeled DNA fragments 128 hybridize to both genomic and proviral sequences on the array. As described above, the hybridization of the unenriched fragments 128 to the proviral sequences on the array indicates the presence of proviral DNA in the sample. The second labeled DNA fragments 136, enriched by immunoprecipitation with RNA polymerase II, hybridize to genomic sequences and to proviral sequences on the array. This indicates productive retroviral infection because the viral DNA is being actively transcribed.

Figure 6:
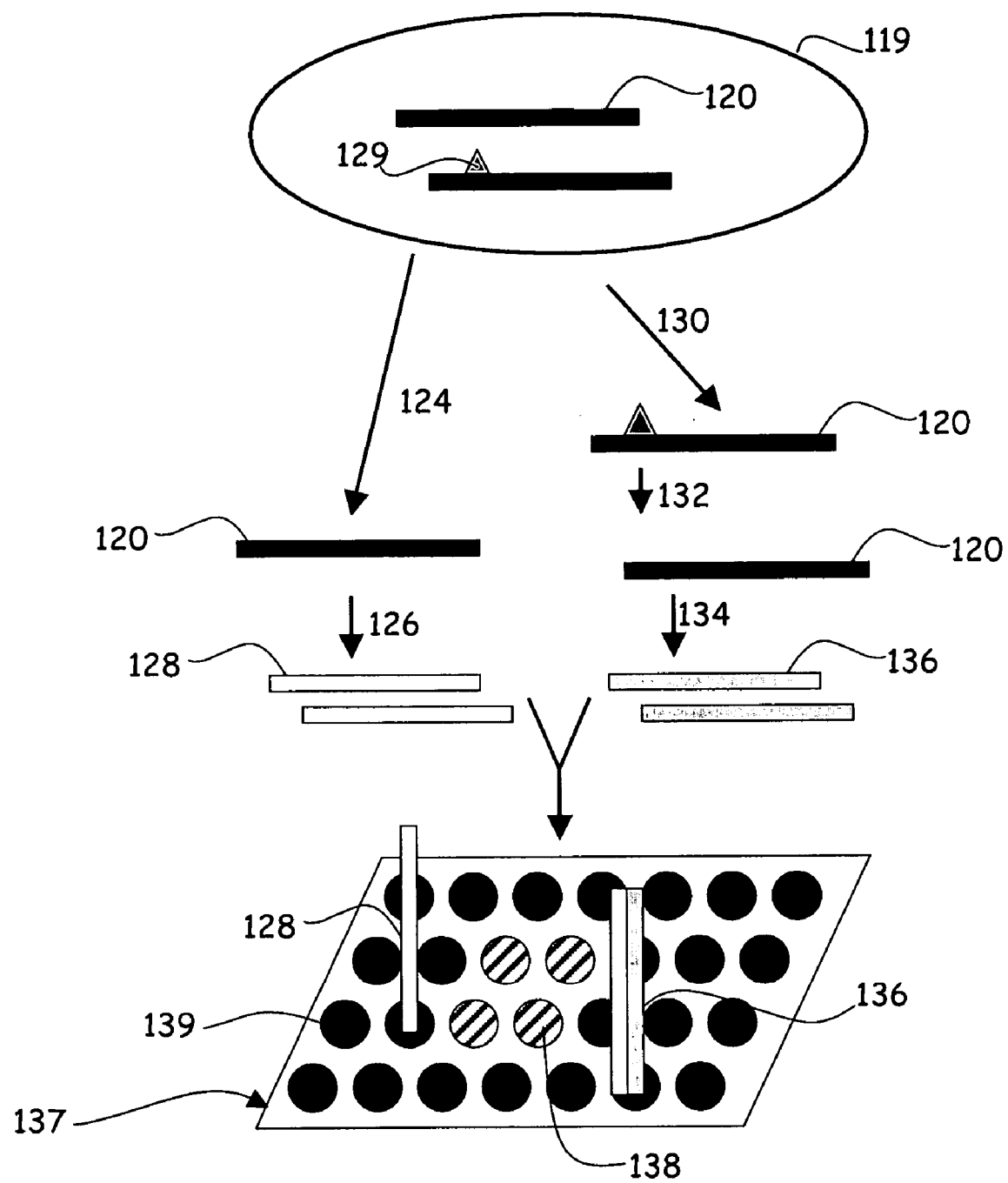
FIG. 6 shows a graphical illustration of the method, as provided herein, in a cell where there is no viral infection.

In an embodiment, no viral infection is detected in a sample comprising genomic DNA according to the method illustrated in FIG. 6. The sample DNA 119 being tested contains both host (genomic) DNA 120 and proviral DNA 122. A first portion of the sample DNA is amplified (represented by arrow 124), and labeled with a first label (arrow 126) resulting in first labeled DNA fragments 128. A second portion of the sample DNA is cross-linked to DNA-bound proteins including RNA polymerase II 129 and immunoprecipitated with an anti-RNA Polymerase II antibody (arrow 130). Following immunoprecipitation, the cross-links are reversed and the DNA fragments are amplified (arrow 132). The amplified DNA is labeled with a second label (arrow 134), resulting in second labeled DNA fragments 136. The first labeled DNA fragments 128 and the second labeled DNA fragments 136 are pooled and hybridized to an array 137 including both proviral sequences 138 and genomic sequences 139.

Where sample DNA 119 is from a host that has too low a level retroviral infection to be detectable, both the first labeled DNA fragments 128 (unenriched) and second labeled DNA fragments 136 (enriched) hybridize only to genomic DNA on the array. This indicates no proviral DNA is detected.

In another embodiment, the methods are used to detect the integration of proviral DNA into genomic DNA. DNA binding proteins are crosslinked to proviral DNA (if any) and genomic DNA in a cell. In a part of the sample, DNA fragments are enriched by immunoprecipitation with an antibody against integrase. The cross linking is reversed and using LM-PCR, the enriched DNA is amplified and labeled. The other part of the sample, where the DNA has not been enriched by immunoprecipitation, is subjected to LM-PCR and also labeled. Typically, the enriched and unenriched pools of DNA are differentially labeled. Both enriched and unenriched pools of labeled DNA are probed for genomic and proviral DNA. In a further embodiment, both enriched and unenriched pools of labeled DNA are hybridized to a DNA microarray that contains both proviral sequences and genomic sequences, under stringent conditions.

Figure 7:
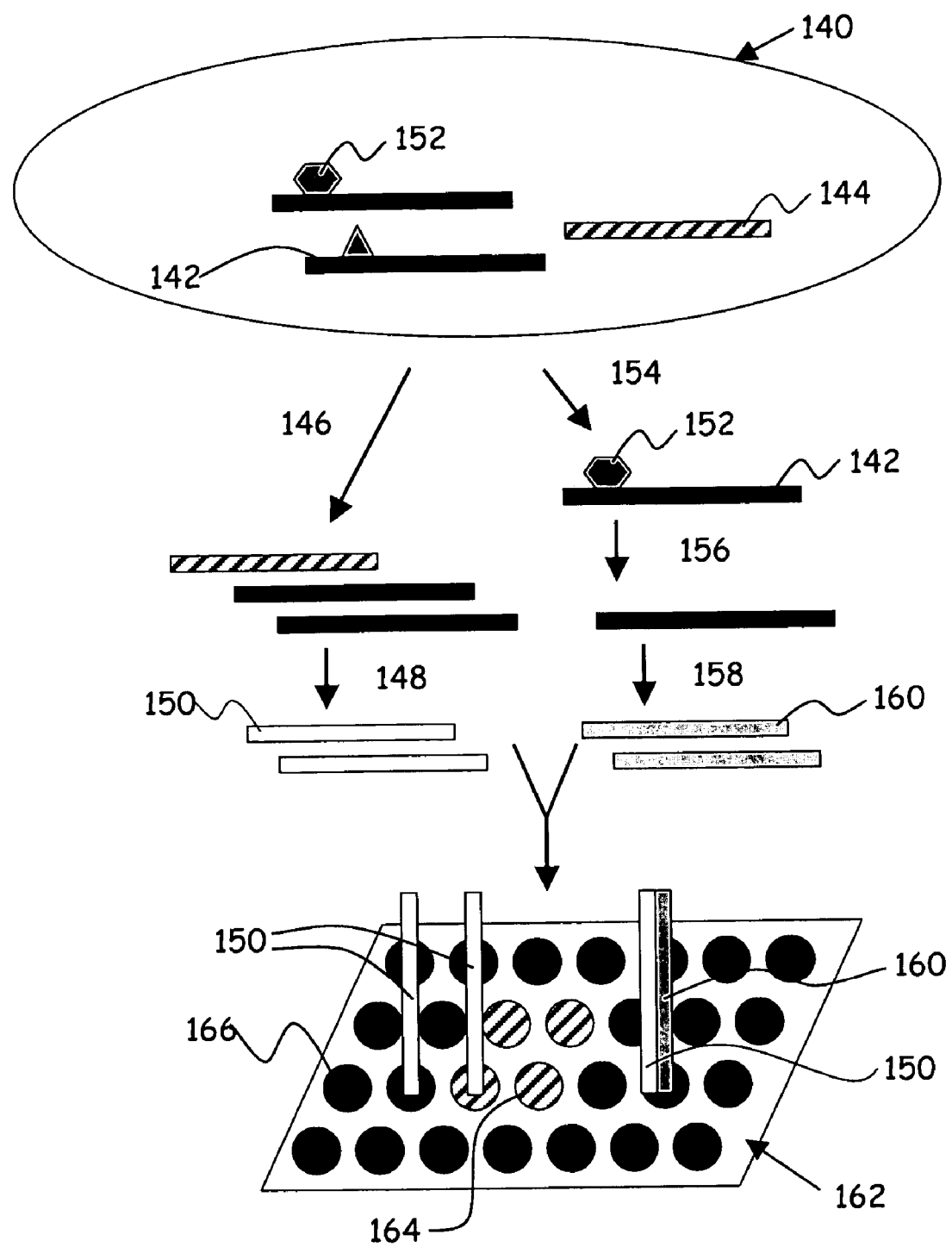
FIG. 7 shows a graphical illustration of a method used to identify a provirus before the provirus is integrated into the host cell and to determine the genomic location of the integration event.
Figure 8:
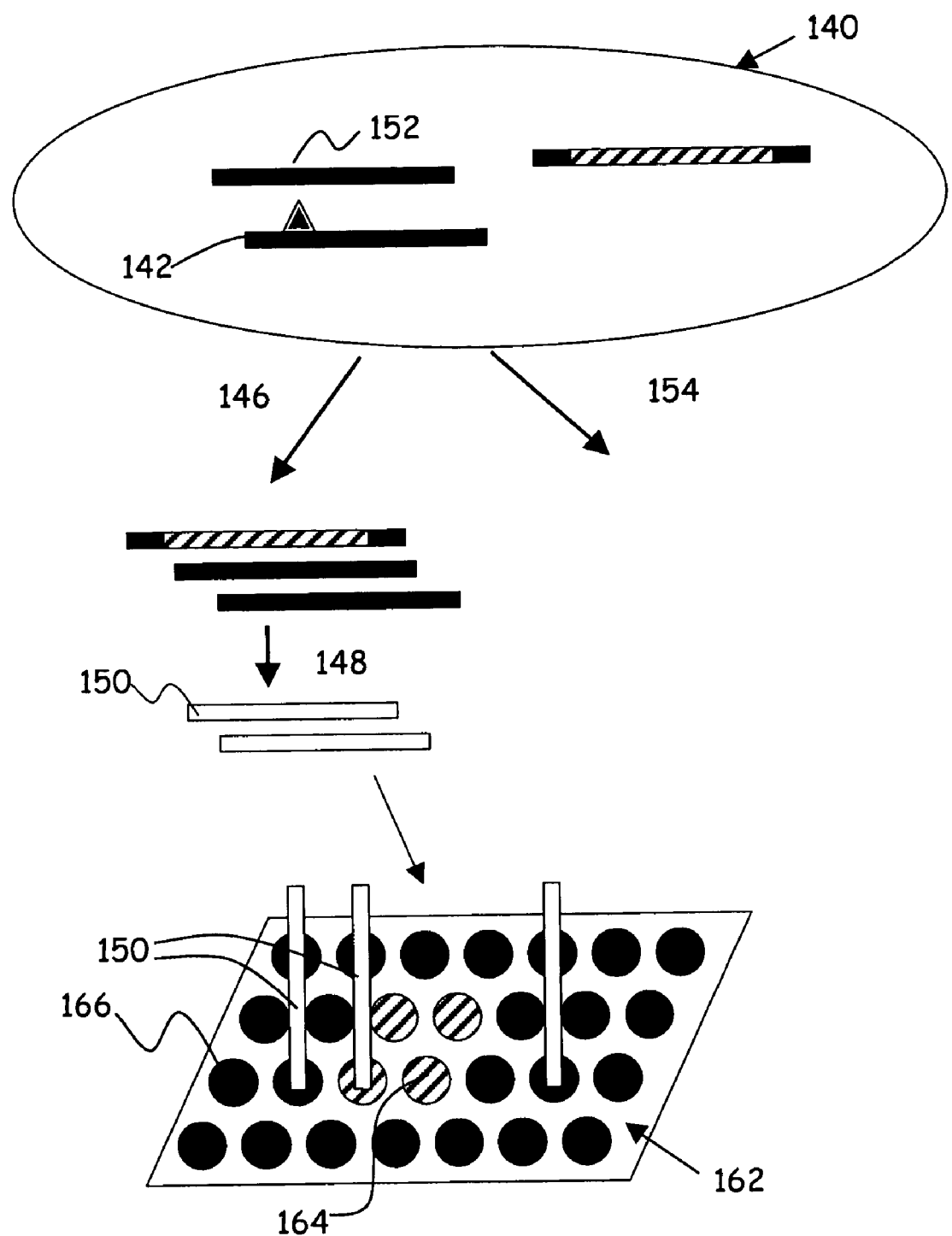
FIG. 8 shows a graphical illustration of a method used to identify a provirus after the provirus is integrated into the host cell and to determine the location of the provirus in the host genome.

One embodiment of this method is illustrated in FIG. 7 (before integration) and FIG. 8 (after integration). Referring first to FIG. 7, sample DNA 140 contains host genomic DNA 142 and provirus DNA 144. A first portion of the sample DNA is amplified (represented by arrow 146), and labeled with a first label (arrow 148) resulting in first labeled DNA fragments 150. A second portion of the sample DNA is crosslinked to DNA-bound integrase 152 and immunoprecipitated with an anti-RNA integrase antibody (arrow 154). Following immunoprecipitation, the cross-links are reversed and the DNA fragments are amplified (arrow 156). The amplified DNA is labeled with a second label (arrow 158), resulting in second labeled DNA fragments 160. The first labeled DNA fragments 150 and the second labeled DNA fragments 160 are pooled and hybridized to an array 162 providing both proviral complementary sequences 164 and genomic complementary sequences 166.

Hybridization of first labeled DNA fragments 150 to both genomic and proviral sequences confirms presence of retrovirus in the sample. Where analysis of the hybridization to the array shows second labeled DNA fragments 160, enriched by integrase-immunoprecipitation, hybridize only to host genomic sequences on the microarray, and not to proviral sequences, integration has not yet taken place. In addition, array hybridization of integrase-enriched DNA fragments 160 provides an effective method for predicting where an integration event will take place, simply by determining the sequence of the hybridized integrase-enriched fragments 160 and comparing to the genomic sequence.

FIG. 8 illustrates a similar method to FIG. 7, however the retrovirus has already integrated into the host genome. Where integration has already taken place, immunoprecipitation with anti-integrase does not result in any DNA fragments. Presence of the retrovirus is confirmed, as in FIG. 7 by hybridization of the unenriched pool of DNA fragments 150 to both genomic and proviral sequences on the array 162. Once the provirus has been integrated into the genome, the DNA fragments do hybridize to proviral DNA sequences on the array, thereby providing an effective method for determining the location of the integration of a provirus.

In practicing embodiments, various methods may be used to enrich or isolate DNA fragments bound to a protein of interest from a mixture that contains both bound DNA fragments and unbound DNA fragments. A general method for examining protein binding to DNA across a genome was disclosed by Wyrick et al., U.S. Pat. No. 6,410,243. In an embodiment, cells are fixed with formaldehyde thereby crosslinking protein bound to DNA to the DNA. The cells are then harvested and sheared by sonication to produce DNA fragments of about 1 kb. The fragments are crosslinked to the protein of interest. Different methods can be used to crosslink DNA binding protein to the host cell genomic DNA or to the proviral DNA. In one embodiment, UV light is used as the crosslinking method. In another embodiment, formaldehyde is used to crosslink DNA binding proteins to the genomic DNA or proviral DNA of the host cell. Formaldehyde crosslinking can be reversed by incubating the crosslinked DNA in a solution with a high salt concentration (such as 5.0M NaCl, for example) at about 65° C. for about 4 hours. Chromatin immunoprecipitation (ChIP) as a technique for determining protein-DNA binding events, is described, for example in Solomon et al., *Cell* 53: 937-947 (1988). A genome-wide location analysis based on this technique is described by Ren et al., *Science* 290: 2306-2309 (2000), which is incorporated herein by reference.

In an embodiment, the DNA fragments are enriched by immunoprecipitation, using an antibody (either monoclonal or polyclonal), or an antigen-binding fragment of an antibody that will specifically bind to the protein of interest. In an embodiment, the DNA fragments are isolated by immunoprecipitation with an anti-RNA polymerase II antibody, which is used to selectively separate DNA fragments bound to RNA polymerase. RNA polymerase II is the enzyme transcribing the integrated HIV proviral genome during a productive viral infection. In another embodiment, the DNA fragments are isolated by immunoprecipitation with an antibody against integrase, which can be used to selectively separate DNA fragments bound to integrase, a protein active in causing integration of the proviral DNA into the host genome. Antibodies against RNA polymerase II and integrase are commercially available.

Isolated DNA fragments can be amplified in a number of different ways including, but not limited to, polymerase chain reaction (PCR) methods. Techniques for such amplification are described in *Current Protocols in Molecular Biology*, Ausubel F. M. et al., eds. 1991, the teachings of which are incorporated herein by reference. In a further embodiment, the DNA fragments are amplified using ligation-mediated polymerase chain reaction (LM-PCR), which causes reproducible amplification of even very small amounts of DNA.

Figure 2:
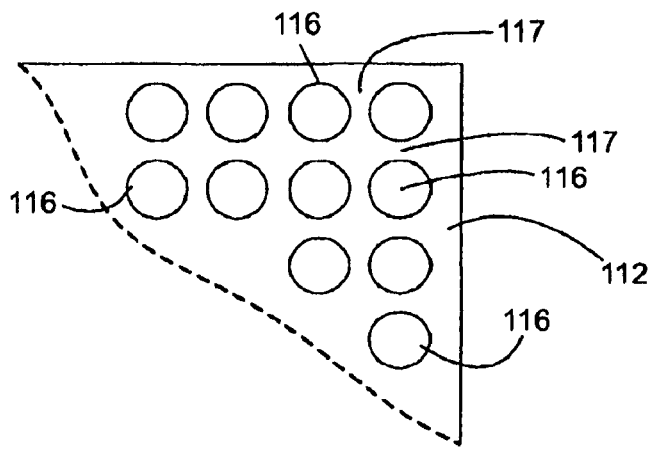
FIG. 2 shows an enlarged view of a portion of FIG. 1 showing spots or features.
Figure 3:
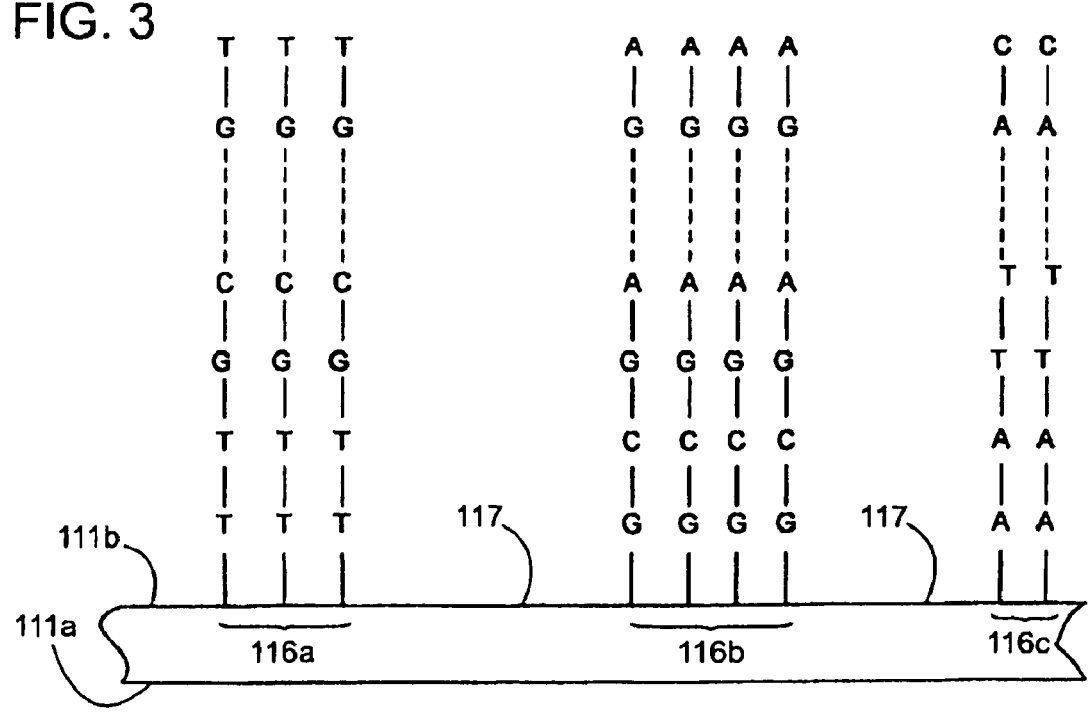
FIG. 3 is an enlarged view of a portion of the substrate of FIG. 1.

The isolated and/or amplified DNA fragments from a sample are probed using DNA that is complementary to the sequence of proviral DNA or host cell genomic DNA using one or more of a number of different techniques. In one embodiment, the complementary sequences are immobilized onto a glass slide or microchip to form a DNA microarray. An exemplary array is shown in FIGS. 1-3, where the array shown in this representative embodiment includes a contiguous planar substrate 110 carrying an array 112 disposed on a rear surface 111b of substrate 110. It will be appreciated though, that more than one array (any of which are the same or different) may be present on rear surface 111b, with or without spacing between such arrays. That is, any given substrate may carry one, two, four or more arrays disposed on a front surface of the substrate and depending on the use of the array, any or all of the arrays may be the same or different from one another and each may contain multiple spots or features. The one or more arrays 112 usually cover only a portion of the rear surface 111b, with regions of the rear surface 111b adjacent the opposed sides 113c, 113d and leading end 113a and trailing end 113b of slide 110, not being covered by any array 112. A front surface 111a of the slide 110 does not carry any arrays 112. Each array 112 can be designed for testing against any type of sample, whether a trial sample, reference sample, a combination of them, or a known mixture of biopolymers such as polynucleotides. Substrate 110 may be of any shape.

As mentioned above, array 112 contains multiple spots or features 116 of biopolymers, e.g., in the form of polynucleotides. All of the features 116 may be different, or some or all could be the same. The interfeature areas 117 could be of various sizes and configurations. Each feature carries a predetermined biopolymer such as a predetermined polynucleotide (which includes the possibility of mixtures of polynucleotides). It will be understood that there may be a linker molecule (not shown) of any known types between the rear surface 111b and the first nucleotide.

Substrate 110 may carry on front surface 111a, an identification code, e.g., in the form of bar code (not shown) or the like printed on a substrate in the form of a paper label attached by adhesive or any convenient means. The identification code contains information relating to array 112, where such information may include, but is not limited to, an identification of array 112, i.e., layout information relating to the array(s), etc.

In an embodiment, the isolated DNA fragments are then hybridized to the microarray under stringent assay conditions. Stringent assay conditions as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions. A stringent hybridization and stringent hybridization wash conditions in the context of nucleic acid hybridization (e.g., as in array, Southern or Northern hybridizations) are sequence dependent, and are different under different experimental parameters.

Stringent hybridization conditions that can be used to identify nucleic acids can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1 M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions that determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no additional" is meant less than about 5-fold more, typically less than about 3-fold more. Other stringent hybridization conditions are known in the art and may also be employed, as appropriate.

The DNA arrays described herein are arrays of nucleic acids, including oligonucleotides, polynucleotides, DNAs, RNAs, synthetic mimetics thereof, and the like. Specifically, the arrays contain spots or features in the form of oligonucleotides corresponding to specific probe sequences. The subject arrays include at least two distinct nucleic acids that differ by monomeric sequence immobilized on, e.g., covalently to, different and known locations on the substrate surface. In an embodiment, the arrays contain spots corresponding to genomic DNA sequences, as well as proviral DNA sequences. In certain embodiments, each distinct nucleic acid sequence of the array is typically present as a composition of multiple copies of the polymer on the substrate surface, e.g., as a spot on the surface of the substrate. The number of distinct nucleic acid or oligonucleotide sequences, or spots or similar structures present on the array may vary, but is generally at least 2, usually at least 5 and more usually at least 10, where the number of different spots on the array may be as a high as 50, 100, 500, 1000, 10,000 or higher, depending on the intended use of the array. The spots of distinct oligonucleotide sequences present on the array surface are generally present as a pattern, where the pattern may be in the form of organized rows and columns of spots, e.g., a grid of spots, across the substrate surface, a series of curvilinear rows across the substrate surface, e.g., a series of concentric circles or semi-circles of spots, and the like. The density of spots present on the array surface may vary, but will generally be at least about 10 and usually at least about 100 spots/cm$^2$, where the density may be as high as $10^6$ or higher, but will generally not exceed about $10^5$ spots/cm². In other embodiments, the oligonucleotide sequences are not arranged in the form of distinct spots, but may be positioned on the surface such that there is substantially no space separating one polymer sequence/feature from another.

Arrays can be fabricated using drop deposition from pulsejets of either polynucleotide precursor units (such as monomers) in the case of in situ fabrication, or the previously obtained polynucleotide. In an embodiment, the arrays are fabricated using oligonucleotides with sequences complementary to proviral DNA or host cell genomic DNA. In another embodiment, separate arrays are fabricated, containing either probes for proviral DNA or host cell genomic DNA. Methods for array fabrication are described in detail in, for example, U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. These references are incorporated herein by reference. Other drop deposition methods can be used for fabrication.

In embodiments, the methods described herein can be used in kits for the identification or detection of viral nucleic acids. The kits contain at least one suitably packaged microarray with spots corresponding to probes for proviral DNA and host cell genomic DNA. In embodiments, the kits described herein contain antibodies or antigen-binding fragments specific for actively transcribed viral proteins, such as RNA polymerase II, viral reverse transcriptase, or viral integrase, for example. The kits may also contain instructions providing information on use of the microarray to detect the presence of viral nucleic acids. In embodiments, the kits also contain fluorophores for differential labeling of enriched and unenriched DNA, reagents for amplifying DNA fragments using PCR, etc.

The various embodiments described above are provided by way of illustration only and should not be construed to limit the claims. Those skilled in the art will readily recognize various modifications and changes that may be made without following the example embodiments and applications illustrated and described herein, and without departing from the true spirit and scope of the following claims.

The invention claimed is:

1. A method of determining whether a viral nucleic acid is present in a host cell, comprising the steps of:
   (a) producing a fragmented DNA sample from the host cell;
   (b) preparing a first target population of nucleic acids from a first portion of said fragmented DNA sample that is enriched for DNA fragments bound to DNA-binding protein, wherein said preparing comprises immunoprecipitation with an antibody or antigen-binding fragment of an antibody specific for the DNA-binding protein, wherein said immunoprecipitation is with an antibody or antigen-binding fragment of an antibody specific for RNA polymerase II;
   (c) preparing a second target population of nucleic acids from a second portion of said fragmented DNA sample wherein said second target population of nucleic acids is a non-enriched portion; and
   (d) contacting the first and second populations of target nucleic acids to an array of probe oligonucleotides, the array comprising probes specific for genomic DNA of the host cell and probes specific for viral nucleic acid; and
   (e) comparing hybridization of said first and second population of target nucleic acids to said array of probe oligonucleotides, wherein hybridization of the second target population of nucleic acids to probes specific for viral nucleic acid is indicative of a viral infection and hybridization of the first target population of nucleic acids to probes specific for viral nucleic acid is indicative of a productive viral infection and wherein lack of hybridization of the first target population of nucleic acids to probes specific for viral nucleic acid is indicative of a latent viral infection.

2. The method of claim 1, wherein the host cell is a mammalian host cell.

3. The method of claim 1, wherein the enriched DNA fragments are labeled with a fluorophore.

4. A method of determining whether a viral nucleic acid is present in a host cell, comprising the steps of:
   (a) producing a fragmented DNA sample from the host cell;
   (b) preparing a first target population of nucleic acids from a first portion of said fragmented DNA sample that is enriched for DNA fragments bound to DNA-binding protein, wherein said preparing comprises immunoprecipitation with an antibody or antigen-binding fragment of an antibody specific for the DNA-binding protein, wherein said immunoprecipitation is with an antibody or antigen-binding fragment of an antibody specific for viral integrase;
   (c) preparing a second target population of nucleic acids from a second portion of said fragmented DNA sample wherein said second target population of nucleic acids is a non-enriched portion; and
   (d) contacting the first and second populations of target nucleic acids to an array of probe oligonucleotides, the array comprising probes specific for genomic DNA of the host cell and probes specific for viral nucleic acid; and
   (e) comparing hybridization of said first and second population of target nucleic acids to said array of probe oligonucleotides, wherein hybridization of the first target population of nucleic acids to probes specific for genomic DNA is indicative of the location of integration of the viral DNA into the genome, and wherein hybridization of the second target population to probes specific for viral nucleic acid and lack of hybridization of the first target population to probes specific for genomic DNA is indicative of viral integration.

5. A method of determining whether a viral nucleic acid is present in a host cell, comprising the steps of:
   (a) producing a fragmented DNA sample from the host cell;
   (b) preparing a first target population of nucleic acids from a first portion of said fragmented DNA sample that is enriched for DNA fragments bound to DNA-binding protein, wherein said preparing comprises immunoprecipitation with an antibody or antigen-binding fragment of an antibody specific for RNA polymerase II;
   (c) preparing a second target population of nucleic acids from a second portion of said fragmented DNA sample wherein said second target population of nucleic acids is a non-enriched portion; and
   (d) contacting the first and second populations of target nucleic acids to an array of probe oligonucleotides, the array comprising probes specific for genomic DNA of the host cell and probes specific for viral nucleic acid; and (e) detecting hybridization of said first and second population of target nucleic acids to said array of probe oligonucleotides to determine whether said viral nucleic acid is present in said cell and wherein lack of hybridization of the first and second target population of nucleic acids to probes specific for viral nucleic acid is indicative of no viral infection.

6. The method of claim 4, wherein the host cell is a mammalian host cell.

7. The method of claim 4, wherein the enriched DNA fragments are labeled with a fluorophore.

8. The method of claim 5, wherein the host cell is a mammalian host cell.

9. The method of claim 5, wherein the enriched DNA fragments are labeled with a fluorophore.

* * * * *